United States Patent [19]

Hinnenkamp et al.

[11] Patent Number: 4,670,474
[45] Date of Patent: Jun. 2, 1987

[54] SYNTHETIC CRYSTALLINE METALLOSILICATE COMPOSITIONS, THE PREPARATION THEREOF AND THEIR USE IN THE CONVERSION OF SYNTHESIS GAS TO LOW MOLECULAR WEIGHT HYDROCARBONS

[75] Inventors: James A. Hinnenkamp; Vernon V. Walatka, both of Cincinnati, Ohio

[73] Assignee: National Distillers and Chemical Corporation, New York, N.Y.

[21] Appl. No.: 750,219

[22] Filed: Jul. 1, 1985

Related U.S. Application Data

[63] Continuation-in-part of Ser. No. 256,299, Apr. 22, 1981, abandoned, which is a continuation-in-part of Ser. No. 92,127, Nov. 7, 1979, Pat. No. 4,331,641.

[51] Int. Cl.[4] .............................................. C07C 1/04
[52] U.S. Cl. .................................. 518/713; 518/714; 518/721
[58] Field of Search ...................... 518/721, 713, 714

[56] References Cited

U.S. PATENT DOCUMENTS 4,086,262  4/1978  Chang et al. .................... 518/719
4,255,349  3/1981  Butter et al. .................... 518/719
4,337,176  6/1982  Boersma et al. ............. 518/719 UX Primary Examiner—Howard T. Mars
Attorney, Agent, or Firm—Kenneth D. Tremain

[57] ABSTRACT

Crystalline palladium or platinum ferrometallosilicate compositions are prepared from a silica-containing mixture by digesting a reaction mixture comprising (a) a tetraalkylammonium compound, (b) a sodium hydroxide, (c) a titanium compound, an aluminum compound, or a manganese compound, (d) an oxide of silicon, (e) an iron ion source, (f) optionally, a chelating agent and (g) water to provide a crystalline ferrometallosilicate which is then palladium or platinum ion-exchanged. Conversion of synthesis gas to low molecular hydrocarbons with high $C_2$-$C_3$ alkanes selectivity employing these new ferrometallosilicates as catalysts is also disclosed.

10 Claims, No Drawings

SYNTHETIC CRYSTALLINE METALLOSILICATE COMPOSITIONS, THE PREPARATION THEREOF AND THEIR USE IN THE CONVERSION OF SYNTHESIS GAS TO LOW MOLECULAR WEIGHT HYDROCARBONS

CROSS-REFERENCE TO RELATED APPLICATIONS

This application is a continuation-in-part of application Ser. No. 256,299 filed Apr. 22, 1981 which is a continuation-in-part of application Ser. No. 092,127, filed Nov. 7, 1979, now U.S. Pat. No. 4,331,641.

BACKGROUND OF THE INVENTION 1. Field of the Invention

The present invention relates to new crystalline silicate compositions. Further, this invention relates to methods for producing these new crystalline metal silicate compositions and to a method for the catalytic conversion of synthesis gas to low molecular weight hydrocarbons utilizing these compositions. 2. Discussion of the Prior Art Zeolite materials, both natural and synthetic, are known to have catalytic capability for various types of reactions, especially hydrocarbon conversions. The well known crystalline aluminosilicate zeolites are commonly referred to as "molecular sieves" and are characterized by their highly ordered crystalline structure and uniformly dimensioned pores, and are distinguishable from each other on the basis of composition, crystal structure, adsorption properties and the like. The term "molecular sieves" is derived from the ability of the zeolite materials to selectively adsorb molecules on the basis of their size and form.

The processes for producing such crystalline synthetic zeolites are well known in the art. A family of crystalline aluminosilicate zeolites, designated ZSM-5, is disclosed in U.S. Pat. No. 3,702,886, said patent being herein incorporated by reference.

U.S. Pat. No. 3,941,871 relates to novel crystalline metal organosilicates which are essentially free of Group IIIA metals, i.e., aluminum and/or gallium. This patent is herein incorporated by reference. It is noted therein that the amount of alumina present in the known zeolites appears directly related to the acidity characteristics of the resultant product and that a low alumina content has been recognized as being advantageous in attaining a low degree of acidity which in many catalytic reactions is translated into low coke making properties and low aging rates. A typical procedure for making the organosilicates is to react a mixture containing a tetraalkylammonium compound, sodium hydroxide, an oxide of a metal other than a metal of Group IIIA, an oxide of silicon, and water until crystals of said metal organosilicates are formed. It is also noted in the patent that the family of crystalline metal organosilicates have a definite X-ray diffraction pattern which is similar to that for the ZSM-5 zeolites. Minor amounts of alumina are contemplated in the patent and are attributable primarily to the presence of aluminum impurities in the reactants and/or equipment employed.

U.S. Pat. No. 3,884,835 discloses crystalline silica compositions. The crystalline silica materials may also contain a metal promoter which may be selected from Group IIIA, Group VB or Group VIB elements. Boron is disclosed as one of the metal promoters.

U.S Pat. No. 4,088,605 is directed to the synthesis of a zeolite, such as ZSM-5, which contains an outer shell free from aluminum. The patent states at column 10, the paragraph beginning at line 20, that to produce the outer aluminum-free shell, it is also essential that the reactive aluminum be removed from the reaction mixture. It is therefore necessary, as noted therein, to process the zeolite and to replace the crystallization medium with an aluminum-free mixture to obtain crystallization of $SiO_2$ on the surface of the zeolite which can be accomplished by a total replacement of the reaction mixture or by complexing from the original reaction mixture any remaining aluminum ion with reagents such as gluconic acid or ethylenediaminotetraacetic acid (EDTA).

Crystalline borosilicate compositions are disclosed in German Offenlegungschrift No. 2,746,790. This application relates specifically to borosilicates which are prepared using the usual procedures for making the aluminosilicate zeolites. It is noted therein that in instances where a deliberate effort is made to eliminate aluminum from the borosilicate crystal structure because of its adverse influence on particular conversion processes, the molar ratios of $SiO_2/Al_2O_3$ can easily exceed 2000–3000 and that this ratio is generally only limited by the availability of aluminum-free raw materials.

German Offenlegungschrift No. 2,755,770 (corresponding British Pat. No. 1,555,928), discloses the preparation of crystalline iron silicates with and without added aluminum, and discloses their use as catalysts for the conversion of methanol to hydrocarbons at high aromatic selectivity. It is further claimed that promoter such as boron can be added to these iron silicates, but no examples of such are given.

U S. Pat. No. 4,468,474 discloses hydrogen activated catalyst compositions comprising iron, silicon and carbon that selectively convert gaseous mixtures to $C_2$–$C_6$ alkanes. It is further noted that the catalysts maintained their activity and high selectivity over a long period and that regeneration of partially deactivated catalysts can be accomplished by treatment with hydrogen at elevated temperature.

U.S. Pat. No. 4,298,695 discloses the conversion of synthesis gas to a liquid hydrocarbon, i.e. naphtha. The process does not employ catalysts which need promoters. High activity without aging is characteristic of the process.

U.S. Pat. No. 4,418,155 discloses a process for the conversion of synthesis gas utilizing a catalyst which comprises a ZSM-5 type zeolite and a carbon oxide reducing component. This process yields a particular product, i.e. linear alpha-olefins, ($C_4$–$C_6$ olefins).

While the art has provided zeolitic catalysts having a wide variety of catalytic and adsorbtive properties, the need still exists for crystalline materials having different and/or enhanced catalytic properties. For example, an important use for a catalytic material is the conversion of synthesis gas to low molecular weight hydrocarbons. Further, many hydrocarbon conversion processes are performed employing zeolites, i.e. alkylation and isomerization. As is well-known in the art, it is important to maximize selectivity for a desired product.

Accordingly, it is one object of the present invention to provide novel crystalline metal silicate compositions.

Another object of this invention is to provide novel crystalline ferrometallosilicate compositions having different and enhanced catalytic properties.

A further object of the invention herein is to provide a method for the preparation of these novel crystalline ferrometallosilicate compositions.

A still further object of this invention is to provide an improved method for the conversion of hydrocarbons and oxygenated compounds to selected end products.

Still another object of this invention is to provide an improved method for the conversion of synthesis gas to low molecular weight hydrocarbons utilizing ferrometallosilicate compositions.

The achievement of these and other objects will be apparent from the following description of the subject invention.

SUMMARY OF THE INVENTION

These and other objects are achieved by incorporating platinum or palladium, preferably palladium, into ferrometallosilicates of the present invention. Briefly, this invention relates to novel palladium ferrometallosilicate compositions, the preparation of these compositions and the use of these compositions to convert synthesis gas to low molecular weight hydrocarbons, preferably $C_{2-3}$ alkanes.

Consequently, when compositions prepared in accordance with the present invention are used in the conversions of synthesis gas to low molecular weight hydrocarbons, the compositions exhibit high catalytic activity in the conversion of synthesis gas to $C_2$–$C_4$ alkanes, with high selectivity specifically for $C_2$–$C_3$ alkanes. These properties are contrary to the results expected from this type of crystalline zeolite composition.

In particular, this invention relates to compositions which are represented in terms of the mole ratio as follows:

(0.2 to 15)$M_{\frac{2}{m}}O$: (0.2 to 10)$Z_{\frac{2}{z}}O$: (5 to 1000)$SiO_2$:

$Fe_{\frac{2}{n}}O$: (0 to 2000)$H_2O$ wherein M comprises a cation of a quaternary ammonium, metal, ammonium, hydrogen and mixtures thereof, m is the valence of said cation, n is the valence of the ferro cation, Z is a cation selected from Group IIIA, IVB, and VIIB, preferably aluminum, titanium or manganese and z is the valence of the Z cation. These compositions are further described by the following additional steps:

wherein said composition contains ion-exchanged palladium; and wherein the composition is substantially sodium free.

In another embodiment, the compositions of this invention are prepared by a method which comprises:

(a) heating a reaction mixture capable of forming a crystalline product under conditions effective to provide a crystalline product, said reaction mixture comprising a quaternary ammonium compound, a source of an aluminum oxide, titanium oxide or manganese oxide, an oxide of silicon, an alkali metal hydroxide, a source of iron oxide, and water, and (b) recovering the crystalline product.

In yet another embodiment, this invention relates to ferrometallosilicate compositions that are prepared by the method described above.

Still another embodiment of this invention relates to a method for the conversion of synthesis gas comprising contacting synthesis gas which comprises hydrogen and carbon monoxide with a catalytically effective amount of the silicate compositions described above under conversion conditions effective to provide an ethane selectively of at least 45%, with aluminum or titanium compositions and a $C_3$ alkane selectivity of at least 35% with the manganese composition.

DESCRIPTION OF THE PREFERRED EMBODIMENTS

Thus, in accordance with the present invention, there are provided crystalline ferrometallosilicates which can be identified in terms of the mole ratios of oxides as follows:

(0.2 to 15)$M_{\frac{2}{m}}O$: (0.2 to 10)$Z_{\frac{2}{z}}O$: (5 to 1000)$SiO_2$:

$Fe_{\frac{2}{n}}O$: (0 to 2000)$H_2O$ wherein M is a cation, m is the valence of M, n is the valence of the iron cation and $Z_{2/z}O$ is a Group III A, IV B or VII B metal oxide e.g., manganese oxide, titanium oxide, or aluminum oxide. The $Z_{2/z}O$ component can include other metal oxides in addition to those oxides noted above. In the preferred form, Z is manganese, titanium or aluminum and M is selected from the group consisting of alkali metal, preferably sodium, tetra- alkylammonium, preferably tetrapropylammonium, phosphonium cations having alkyl groups containing up to 6 carbon atoms, preferably 2 to 5 carbon atoms and mixtures thereof.

The ferrometallosilicates of this invention are preferably prepared by heating a reaction mixture comprising a quaternary ammonium compound, e.g. a tetraalkyl (such as tetrapropyl) ammonium bromide or hydroxide, an alkali metal source, e.g. sodium hydroxide, or sodium chloride, a metal, e.g. aluminum, titanium or manganese or a metal compound, e.g. aluminum chloride, titanium chloride or manganese chloride, as the source or metal precursor for the $Z_{2/z}O$, oxide of silicon, a source of ferrous and/or ferric ion, such as a ferrous and/or a ferric salt, e.g. $FeCl_2 \cdot 4H_2O$, $FeCl_3 \cdot 6H_2O$, mixtures thereof and the like, optionally, a chelating agent, e.g. 8-hydroxyquinoline-5-sulfonic acid (8HQS) or urea, and water, usually having the composition in terms of mole ratios falling within the following ranges:

|  | Broad | Preferred |
|---|---|---|
| $OH^-/SiO_2$ | 0.05–3 | 0.20–0.90 |
| $R_4N^+/(R_4N^+ + Na^+)$ | 0.01–1 | 0.03–0.9 |
| $H_2O/OH^-$ | 10–800 | 20–500 |
| $SiO_2/Z_{\frac{2}{z}}O$ | 2–1000 | 12–500 |
| $SiO_2$/chelating agent | >1 | >20 |
| $SiO_2/Fe_{2/n}O$ | 10–10,000 | 40–4000 | and maintaining the mixture at elevated temperatures for a time sufficient to form crystals of the product. Typical reaction conditions consist of heating the reaction mixture at elevated temperature, e.g., 50° to about 250° C., and even higher, for a period of time of from about 6 hours to as much as 60 days. The preferred temperature is from about 100° to 190° C., for time periods of from about 1 to about 16 days. The reaction mixture can be heated at elevated pressure as in an autoclave, or at normal pressure, e.g., as by refluxing.

The preferred method of heating the reaction mixture is at reflux temperature.

As in common practice in the production of silicate compositions, when reflux heating of the reaction mixture is employed, large amounts of sodium chloride along with some sulfuric acid are added to the reaction mixture to ensure crystallization of the product. Thus, in reflux preparation, the ratios of $SiO_2/Z_2O_3$, $OH^-/SiO_2$, $SiO_2/Fe_{2/n}O$ and the like ratios may result in values different from the ratios of the autoclave processing.

The digestion of the gel particles is carried out until crystals form. The solid product is separated from the reaction medium as by cooling the whole to room temperature, filtering, and water washing.

The foregoing product is dried, e.g., at 110° C. for from about 8 to 24 hours or longer. Of course, milder conditions may be employed if desired, e.g., room temperature under vacuum.

The sodium content of these compositions must be minimized in order to obtain an active composition for the conversion of synthesis gas to low molecular weight hydrocarbons. Sodium contamination can be substantially avoided by ion-exchanging ammonium into the sodium ferrometallosilicate composition prior to palladium ion-exchange. Sodium content in the ferrometallosilicate composition in the range of about 0.5 to about 1.0 wt. % renders the composition inactive for the conversion of synthesis gas to low molecular hydrocarbons. However, subsequent to ammonium ion-exchange, an active composition is obtained when the sodium content is in the range of about 0 to about 0.4, preferably in the range of about 0 to about 0.05 wt. %

The ferrometallosilicates of the present invention are palladium exchanged and heat treated in air at 540° C. for 4 hours and then cooled to ambient temperature. The ferrometallosilicates are subjected to a hydrogen treatment during which the treating temperature is increased from ambient conditions to about 200° C. to about 500° C., preferably about 300° C. to about 400° C. The rate of temperature increase must be controlled. A temperature increase of about 0.1° C. to about 5.0° C. per minute, preferably about 0.5° C. to about 2.0° C. per minute, must be employed. After reaching the desired temperature, the composition is maintained at this temperature for about 0.5 to about 4 hours, preferably about 0.75 hours to about 1.25 hours. The composition is then cooled to ambient temperature in the presence of an inert gas or hydrogen. The treatment of the composition with hydrogen during the heat treatment and cooling steps increases the $C_2$ or $C_3$ alkane selectivity when the composition is employed in the conversion of synthesis gas to low molecular weight hydrocarbons.

The ferrometallosilicate compositions of the present invention can be extracted with a strong mineral acid to further enhance ethane selectivity prior to incorporation of palladium or platinum. This extraction with a strong mineral acid is believed to remove non-lattice or amorphous iron that is detrimental to $C_2$ or $C_3$ alkane selectivity. Any strong mineral acid can be used for this extraction procedure, such as for example, hydrochloric acid, sulfuric acid, nitric acid or the like. The strong mineral acids should have a concentration in the range of about 0.1 molarity up to and including the concentrated form of the acid. The extraction treatment should take place prior to palladium exchange for at least 1 hour to about 48 hours at a temperature in the range of about 0° C. to about 100° C., preferably about 60° C.

Further, $C_2$ or $C_3$ alkane selectivity of the composition will vary with the amount of iron present in the lattice structure. For example, high $C_2$ or $C_3$ alkane selectivity is obtained at 0.1% to about 2.0% iron. In the preferred form, the composition has a higher $C_2$ alkane selectivity and better stability when iron is present in the lattice structure in the range of about 0.3% wt. to about 0.8% wt.

In an optional embodiment of this invention, the physical mixing of commerically available methanol synthesis catalysts, such as for example, a copper oxide-zinc oxide or a chromium oxide-zinc oxide catalyst with the palladium ferrometallosilicate increases the catalytic conversion of synthesis gas to $C_{2-3}$ alkanes. The copper-zinc catalyst, available from United Catalyst Inc. under the designation "C18HC", has high activity due to its composition of a 1:1 ratio of ZnO to CuO plus 10% alumina. The chromium-zinc catalyst, available from Harshaw Chemical Co. under the designation "Zn-0312 T," is composed of 74% ZnO, 21% chromium oxide and 600 parts per million of aluminum. Higher yields result when the methanol synthesis catalyst is added in a weight ratio of about 0.1 to 10, preferably about 0.3 to 5, in relation to the amount of palladium ferrometallosilicate.

The methanol synthesis catalyst may be physically mixed with the palladium ferrometallosilicate composition by any known method, such as for example, blending, ultrasonic mixing and the like.

As noted hereinabove, and as known in the art, the procedure for preparing zeolites, e.g., alumino-silicates, is well known. It is an optional feature of the present invention, however, that the crystalline composition can be prepared using a reaction mixture containing a chelating agent, such as 8-hydroxy-quinoline-5-sulfonic acid or urea, in a molar ratio $SiO_2$/ chelating agent of greater than 1, preferably greater than 20.

While 8-hydroxyquinoline-5-sulfonic acid is a preferred chelating agent for the preparation of the crystalline ferrometallosilicates of this invention, other chelating agents, such as urea, which can provide crystalline materials are also contemplated to be within the scope of this optional embodiment of the invention.

The present invention provides a crystalline palladium ferrometallosilicate composition which exhibits superior catalytic activity for the highly selective conversion of mixtures of synthesis gas (carbon monoxide and hydrogen) to low molecular weight hydrocarbons ($C_2$–$C_4$ alkanes). Moreover, the compositions of the present invention maintain their catalytic activity and high selectivity over relatively long periods of time.

Synthesis gas is provided commercially by such well known processes as the steam reforming of naphtha or natural gas or the partial oxidation of carbonaceous materials, such as coal or heavy petroleum distillates. The reactions involved are:

Steam Reforming:

$$C_nH_{(2n+2)} + nH_2O \rightarrow nCO + (2n+1)H_2$$

Partial Oxidation $$4C + 2H_2O + O_2 \rightarrow 2H_2 + 4CO$$

or $$C_nH_{(2n+2)} + (n/2)O_2 \rightarrow nCO + (n+1)H_2$$

The high activity exhibited by the palladium exchanged silicates of this invention for the conversion of synthesis gas to low molecular weight hydrocarbons, especially ethane and propane, is particularly surprising in view of the inactivity of ferrometallosilicate compositions that have not been palladium ion-exchanged. Further, the selectivity for ethane or propane in the conversion of synthesis gas to low molecular alkanes is unexpected since iron based catalysts are known to possess Fischer-Tropsch activity, e.g. converting synthesis gas to primarily methane or $C_{5+}$ hydrocarbons.

The process for conversion of mixtures of gaseous carbon monoxide and hydrogen in the presence of an effective amount of the compositions of the present invention is conveniently conducted at a temperature in the range of about 250° to about 500° C., normally 325°–500° C., a pressure in the range of about 0 psig (101 kPa) to about 1500 psig (10,446 kPa), preferably 50 psig (446 kPa) to about 1000 psig (6995 kPa) in a batch or flow reactor system. The volume ratio of carbon monoxide to hydrogen is conveniently in the range of 0.2 to about 6, normally about 0.5 to about 2.

The process of the present invention is conducted for a time sufficient to form a product mixture, containing methane, $C_2$–$C_6$ alkenes and alkanes, carbon dioxide, water and less than 5.0% alcohols and ethers. The product mixture may be entrapped in a suitable trapping means such as a condenser and thereafter separated by standard techniques, e.g. distillation. For example, when utilizing the subject process in a batch-wise fashion, contact times of about 0.1 to about 30 minutes, preferably about 0.5 to about 2 minutes are found to be effective. When reacting the subject process continuously, space velocities of about 0.1 to about 20, preferably about 0.5 to about 10 weight hourly space velocity (WHSV) should be utilized.

The activity of the compositions of the present invention is achieved at temperatures of about 325°–500° C. Within this range, the composition deactivates rapidly at temperatures of about 450° C. to about 500° C. The activity of the composition is lower at temperatures of about 300° C. to about 325° C. Temperatures in the range of about 325° C. to about 425° C. are preferred for maximizing catalytic activity, service lifetime and selectivity for $C_2$–$C_4$ alkanes.

The process of the present invention can be operated in batch or continuous mode. A continuous flow reactor minimizes secondary reactions of initially formed products and extends the service lifetime of the compositions.

It is not known why the crystalline compositions of this invention provide such unexpected properties as high activity for the conversion of synthesis gas to low molecular weight hydrocarbons and the high selectivity for $C_2$ or $C_3$ alkanes. Crystalline compositions that do not contain both iron and palladium do not inherently exhibit these properties and cannot be activated to provide a crystalline composition having the selectivity described herein. It is believed that the inability of the iron silicates which do not contain palladium to catalyze synthesis gas conversion is because the iron is part of the lattice structure and is not readily reduced to the synthesis gas active metal as is the case with amorphous iron catalysts.

In preparing the crystalline compositions of this invention, the silica source can be any of those commonly considered for use in synthesizing zeolites such as powdered silicic acid, colloidal silica or dissolved silica. A preferred silica source is Cab-O-Sil, sold by Cabot Co.

The metallic oxide material employed in the preparation mixture may include one or more oxides of Group IIIA, Group IVB and Group VIIB elements. The preferred metals are manganese, titanium and aluminum. The source for manganese may be manganese chloride, manganese sulfate, or manganese nitrate, the source for titanium may be titanium chloride and the source for aluminum may be aluminum chloride or aluminum hydroxide, among others and the like.

The source of iron oxide in the preparation mixture may be ferrous salts or ferric salts such as $FeCl_2 \cdot 4H_2O$, $FeCl_3 \cdot 6H_2O$ and the like as well as mixtures of such salts.

The specific crystalline compositions of this invention described, when evaluated for catalytic properties without having been calcined, are inactive, possibly because the intracrystalline free space is occupied by organic cations from the forming solution. They may, however, be activated by heat treatment using known techniques such as heating in an inert atmosphere or air at 200°–900° C., for 1 to 60 hours. This may be followed by ion-exchange with ammonium salts and further heat treatment at 200°–900° C.

Typical ion-exchange techniques include contacting the members of the family of ferrometallosilicates with a salt solution of the desired replacing cation or cations. Although a wide variety of salts can be employed, particular preference is given to chlorides, nitrates and sulfates. The salt solution exchange takes place prior to palladium exchange in order to minimize sodium contamination as described above.

Representive ion-exchange techniques are disclosed in a wide variety of patents including U.S. Pat. Nos., 3,140,249, 3,140,251 and 3,140,253, which are incorporated herein be reference.

Alternatively, the ferrometallosilicate may be impregnated with an aqueous or ammonia containing solution of palladium or platinum salt. The ammonia solvent which is used may be liquid ammonia or aqueous ammonia containing greater than 50 weight percent ammonia. Prior to impregnation with either solution, the ferrometallosilicate should, if necessary, be calcined at about 300° C. to about 600° C. for at least 4 hours in an inert atmosphere to drive off any organic cations which remain after formation of the ferrometallosilicate and which would tend to block the pore structure of the ferrometallosilicate.

Addition of the ammonia solvent dissolves the palladium or platinum salt and the resulting solution then permeates the ferrometallosilicate to impregnate the ferrometallosilicate with palladium or platinum. After impregnation, the ferrometallosilicate is dried, generally under mild conditions, to drive off the solvent and fix the palladium or platinum on the ferrometallosilicate. Temperatures of up to about 200° C., preferably about 110° C. to about 130° C. are suitable for this purpose.

The percent by weight of palladium or platinum that is ion-exchanged or impregnated significantly affects the catalytic activity and selectivity for $C_2$–$C_3$ alkanes in the conversion of synthesis gas. The lower the percent by weight of palladium or platinum present in the ferrometallosilicate, generally the lower the catalytic activity for the conversion of synthesis gas to $C_2$–$C_3$ alkanes and a corresponding lower selectivity of $C_2$–$C_3$ alkanes. The percent by weight of palladium or platinum present in the ferrometallosilicate should be about 0.1% weight to about 10% weight, with about 0.2% weight to about 5.0 % weight being preferred. The ferrometallosilicate must have at least 0.1% weight of palladium or platinum present in the composition in order obtain good selectivity and stability for the conversion of synthesis gas to $C_{2-4}$ alkanes.

Various metals may be ion-exchanged or alternatively, impregnated on the ferrometallosilicates in accordance with this invention. Group VIII metals are intended to be included in the scope of this invention, with palladium or platinum being preferred, and palladium being specifically preferred.

Following contact with the salt solutions of the desired replacing cation, the crystalline compositions are then preferably washed with water and dried at a temperature up to to about 200° C. and thereafter heat treated as previously described.

Regardless of the cations replacing the sodium in the synthesized form of the compositions, the spatial arrangement of the atoms which form the basic crystal lattices in any given composition of this invention remain essentially unchanged by the described replacement of sodium or other alkali metal as determined by taking an X-ray powder diffraction pattern of the ion-exchanged material.

The compositions prepared by the instant invention are formed in a wide variety of particular sizes. Generally speaking, the particles can be in the form of a powder, a granule, or a molded product, such as extrudate having a particle size sufficient to pass through a 2 mesh (Tyler) screen and be retained on a 100 mesh (Tyler) screen. In cases where the composition is molded, such by extrusion, the composition can be extruded before drying or dried or partially dried and then extruded.

In the case of the mixtures of the methanol synthesis catalyst and the palladium ferrometallosilicate, mixing can occur before or after the extrusion process. It should be remembered that when the methanol synthesis catalyst is present before heat treatment that the treating temperature should be chosen so as not to adversely affect the methanol synthesis catalyst.

In the case of many catalysts, it is desired to incorporate the composition of this invention with another material resistant to the temperatures and other conditions employed in organic conversion processes. Such materials include active and inactive materials and synthetic or naturally occurring crystalline compositions as well as inorganic materials such as clays, silica and/or metal oxides. The latter may be either naturally occurring or in the form of gelatinous precipitates or gels including mixtures of silica and metal oxides. Use of a material in conjunction with the present composition tends to improve the conversion and/or selectivity of the composition in certain organic conversion processes. Inactive materials suitably serve as diluents to control the amount of conversion in a given process so that products can be obtained economically and in an orderly manner without employing other means for controlling the rate of reaction. Normally, zeolite materials have been incorporated into naturally occurring clays, e.g., bentonite and kaolin, to improve the crush strength of the composition under commercial operating conditions. These materials, e.g., clays, oxides, etc. function as binders for the composition. It is desirable to provide a composition having good crush strength, because in a chemical process the composition is often subjected to handling or use which tends to break the composition down into powder-like materials which cause problems in processing. These clay binders have been employed for the purpose of improving the crush strength of the composition.

In addition to the foregoing materials, the composition can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel.

The following examples are presented as specific embodiments of the present invention and show some of the unique characteristics of the claimed crystalline compositions and are not to be considered as constituting a limitation on the present invention.

EXAMPLE 1

I. Preparation of Ferrotitanosilicate-Reflux Method

A. Preparation of Precipitation Solutions

1. Sodium Silicate (Basic Solution)

69 grams of 50% (w/w) NaOH solution were added to 750 ml of deionized water and brought to reflux. 400 grams of fumed silica were added and heated until dissolution occurred.

2. Precipitant Solution (Acidic Solution)

25 grams of concentrated $H_2SO_4$ were added to 500 ml of deionized water. 106 grams of NaCl, 41 grams of tetrapropylammonium bromide, and 7 ml of $TiCl_4$ were added to the $H_2SO_4$ solution.

3 Iron Solution 9 grams of Urea were added to 200 ml of deionized water and then 5 grams of $Fe(NO_3)_3 9H_2O$ were added to the solution.

B. Precipitation and Crystallization

The acidic solution ($A_2$) was added at a rate of 4 ml/min. to the rapidly stirred basic solution ($A_1$). The iron solution ($A_3$) was heated to precipitate iron hydroxide. After all of the acidic solution ($A_2$) was added and gelation was completed, the iron solution ($A_3$) was slowly added. The pH of the solution was then adjusted to 8.5 with either $H_2SO_4$ or NaOH. The gelatinous solution was homogenized and transferred to a polypropylene flask and heated at 120° C. for 14 days. After this period, the solid was washed by repetitive decantation with deionized water. The solid was then collected by filtration and dried at 110° C. for 16 hours.

II $Na^+$-Ferrotitanosilicate

The dried solid from step IB was calcined in air by raising the temperature 50° C. every 30 minutes to 540° C. and maintained at this temperature for 16 hours.

III. $NH_4^+$ or $H^+$ Ferrotitanosilicate 50 grams of Na-Ferrotitanosilicate (II) were added to a solution of 25 grams $NH_4Cl$ dissolved in 400 ml deionized water and refluxed for 16 hours. The solution was then decanted and additional solution containing 25 grams $NH_4Cl$ dissolved in 400 ml water deionized were added. After 4 hours of reflux the solid was washed by repetitive decantation and isolated by filtration. Drying at 110° C. overnight yielded $NH_4^+$-Ferrotitanosilicate.

If the H+rrotitanosilicate was desired, the NH$_4$+ form was calcined at 540° C. for 4 hours.

IV. Pd$^{2+}$Ferrotitanosilicate

A. Ion Exchange

A 20 gram sample of either Na+ (II) or NH$_4$+ (III) Ferrotitanosilicate was added to a solution containing 0.6 gram Pd(NH$_3$)$_4$Cl$_2$ dissolved in deionized water. After being stirred at ambient temperature for 16 hours, the liquid was decanted and another 0.6 g Pd(NH$_3$)$_4$Cl$_2$ dissolved in 400 ml deionized water was added. After being stirred at ambient temperature for 4 hours, the solid was washed with deionized water by repeated decantation. The solid was collected by filtration and dried at 110° C. overnight.

B. Catalyst Pretreatment

Before charging Pd-Ferrotitanosilicate, the preferred pretreatment was to calcine 25 grams of IV A in air at 540° C. for 4 hours and then cool to ambient temperature. The calcined solid was treated with 5% hydrogen in nitrogen at a temperature program of 1° C./minute to 350° C. and held for 1 hour. After being cooled to ambient temperature in 5% hydrogen, a portion of the composition was charged to the reactor.

EXAMPLE 2

A ferromanganosilicate was prepared by the reflux method following the procedure described in Example 1, except that in the precipitant solution (A$_2$) step:

(1) 20 grams of H$_2$SO$_4$ were substituted for 25 grams of H$_2$SO$_4$, (2) 12 grams of Mn(NO$_3$)$_2$ 50% aq. and 7.5 grams of FeCl$_3$ 6H$_2$O were substituted for 7 ml of TiCl$_4$, and (3) 700 ml of deionized water was used instead of 500 ml of deionized water.

Further, the iron solution step was not performed.

EXAMPLE 3

A ferroaluminosilicate was prepared by the reflux method following the procedure described in Example 1, except that in the precipitant solution (A$_2$) step:

(1) 24 grams of H$_2$SO$_4$ were substituted for 25 grams of H$_2$SO$_4$, and (2) 11 grams of Al$_2$(SO$_4$)$_3$ 14H$_2$O were substituted for 7 ml of TiCl$_4$.

Further, in the iron solution (A$_3$) step:

(1) 7.5 grams of FeCl$_3$ 6H$_2$O were substituted for 5.0 grams of Fe(NO$_3$)$_3$ 9H$_2$O (2) 350 ml of deionized water was used instead of 200 ml of deionized water, and (3) 16 grams of 8-hydroxyquinoline-5-sulfonic acid were substituted for 9 grams of urea.

(4) The iron solution was not heated.

Table I shows the quantities of the compounds used in the synthesis of the crystalline ferrometallosilicate compositions of Examples 1-3.

TABLE I

Synthesis of Crystalline SiO$_2$/FeO$_x$/MO$_x$ (Reflux method)

| Precipitation Solutions | Example 1 Ti | Example 2 Mn | Example 3 Al |
|---|---|---|---|
| 1. Sodium Silicate | | | |
| Silica (g) | 100 | 100 | 100 |
| 50 wt % NaOH (g) | 69 | 69 | 69 |
| H$_2$O (l) | 0.75 | 0.75 | 0.75 |
| 2. Precipitant | | | |
| H$_2$SO$_4$ (g) | 25 | 20 | 24 |
| NaCl (g) | 106 | 106 | 106 |
| TPA (g) | 41 | 41 | 41 |
| H$_2$O (l) | 0.50 | 0.70 | 0.50 |
| other (g) | 7 ml. TiCl$_4$ | 12Mn(NO$_3$)$_2$ 50% aq., 7.5 FeCl$_3$.6H$_2$O | 11Al$_2$(SO$_4$)$_3$. 14H$_2$O |
| 3. Iron | | | |
| Fe Salt (g) | 5.0 Fe(NO$_3$)$_3$.9H$_2$O | — | 7.5 FeCl$_3$.6H$_2$O |
| H$_2$O (l) | 0.20 | — | 0.35 |
| 50 wt % NaOH (g) | — | — | 10 |
| other (g) | 9 Urea | — | 16 8HQS |

EXAMPLE 4

I. Preparation of Ferrotitanosilicate-Autoclave Method

A. Preparation of Solutions

1. Sodium Silicate 100 grams of Cab-o-Sil M-5 and 69 grams of NaOH (50% w/w) are dissolved in 750 ml deionized water.

2. Quaternary Ion/Titanium 7 ml of TiCl$_4$ and 41 grams of tetrapropylammonium bromide are dissolved in 500 ml deionized water.

3. Iron Solution 9 grams of urea is dissolved in 200 ml water, and added to 5.0 grams of Fe(NO$_3$)$_3$.9H$_2$O dissolved in 100 ml water.

B. Solution Mixing and Crystallization

The iron solution (A$_3$) is heated at reflux to precipitate hydroxide and then is added to sodium silicate (A$_1$) with rapid stirring. The quaternary ion solution (A$_2$) is then added to the iron/sodium silicate solution. During the addition, the solution turns black. After stirring at ambient temperature overnight, the solution is heated to 170° C. for 7 days without stirring. After 7 days, the solid is washed by successive decantations with deionized water and collected by filtration. The solid is dried at 110° C. overnight.

EXAMPLE 5

A ferromanganosilicate is prepared by the autoclave method following the procedure described in Example 4, except that in the quaternary solution (A$_2$) step:

(1) 12 grams of Mn (NO$_3$)$_2$ 50% aq. and 7.5 FeCl$_3$ 6H$_2$O are substituted for 7 ml of TiCl$_4$, and (2) 700 ml of deionized water is used instead of 500 ml of deionized water.

Further, the iron (A$_3$)step step is not performed.

EXAMPLE 6

A ferroaluminosilicate is prepared by the autoclave method following the procedure described in Example 4, except that in the quaternary solution (A$_2$) step:

(1) 11 grams of Al$_2$(SO$_4$)$_3$ 14H$_2$O are substituted for 7 ml of TiCl$_4$.

In the iron (A$_3$) step:

(1) 16 grams of 8-hydroxyquinoline-5-sulfonic acid are substituted for 9 grams of urea, and (2) 10 grams of NaOH (50% w/w) are added.

Further, in the iron (A$_3$) step:

(1) 7.5 grams of FeCl$_3$ 6H$_2$O are substituted for 5.0 grams of Fe(NO$_3$)$_3$ 9H$_2$O and (2) heating at reflux is not preformed.

Table II shows the quantities of the compounds used in the synthesis of the crystalline ferrometallosilicate compositions of Examples 4–6.

TABLE II

Synthesis of Crystalline SiO$_2$/FeO$_x$/MO$_x$
(Autoclave method)

| Preparation of Solutions | | | |
|---|---|---|---|
| Composition | 4 | 5 | 6 |
| 1. Sodium Silicate | Ti | Mn | Al |
| Cab-o-Sil (g) | 100.0 | 100.0 | 100.0 |
| 50 wt % NaOH (g) | 69.0 | 69.0 | 69.0 |
| H$_2$O (l) | 0.75 | 0.75 | |
| 2. Quaternary Ion | | | |
| TPA (g) | 41.0 | 41.0 | 41.0 |
| H$_2$O (g) | 0.5 | 0.7 | 0.5 |
| other (g) | 7 ml TiCl$_4$ | 12 Mn(NO$_3$)$_2$. 50% aq. | 11 Al$_2$(SO$_4$)$_3$. 14H$_2$O |
| 3. Chelate | | | |
| Urea (g) | 8.0 | — | — |
| H$_2$O (l) | 0.2 | — | 0.4 |
| Other (g) | | | 16 8HQS 10 NaOH (50 wt %) |
| 4. Iron | | | |
| Fe(NO$_3$)$_3$ 9H$_2$O (g) | 5.0 | — | — |
| H$_2$O (l) | 0.1 | — | 0.1 |
| Other (g) | | | 7.5 FeCl$_3$. 6H$_2$O |

EXAMPLE 7

This example compares the catalytic properties of the palladium ferromanganosilicate composition (1) of the present invention to a composition (D) (outside the present invention) for the conversion of synthesis gas. All of the compositions were prepared in accordance with Example 1 and all runs were conducted at 735 psig (5169 kPa) in a 310 stainless steel tubular reactor at an actual hourly space velocity of 80.

TABLE IV

SYNGAS REACTIONS
THE EFFECT OF METALS
ON PALLADIUM FERROSILICATE
Pd—SiO$_x$/FeO$_x$/MO$_x$

| Composition | D | 1 |
|---|---|---|
| M(2) | — | Mn |
| % Fe | 1.5 | 1.1 |
| % Pd | 1.1 | 1.6 |
| % M | 0 | 0.9 |
| HC Yield, % (3) | 13 | 10 |
| HC Sel., % (3) | | |
| C$_1$ | 28 | 16 |
| C$_2$ | 34 | 28 |
| C$_3$ | 28 | 40 |
| C$_4$ | 10 | 17 |
| C$_{5+}$ & Ar | 0 | 0 |
| CO$_2$ Yield (3) | 13 | 12 |

(1) 350° C., H$_2$/CO = 1, 735 psig (5169 kPa), Actual Hourly Space Velocity = 80
(2) Added as salts to composition growth mixture
(3) Based on carbon The data show that composition 1 of the present invention has a higher C$_3$ selectivity than composition D for synthesis gas conversion when tested at 350° C.

EXAMPLE 8

This example compares the catalytic properties of the palladium ferrometallosilicate composition (2 and 3) of the present invention to the composition (D) for the conversion of synthesis gas. All of the compositions were prepared in accordance with Example 1 and all runs were conducted at 735 psig (5169 kPa) in a 310 stainless steel tubular reactor at an actual hourly space velocity of 80.

TABLE V

SYNGAS REACTIONS
THE EFFECT OF METALS
ON PALLADIUM FERROSILICATE
Pd—SiO$_x$/FeO$_x$/MO$_x$(1)

| Composition | D | 2 | 3 |
|---|---|---|---|
| M(2) | — | Al | Ti |
| % Fe | 1.5 | 1.5 | 0.6 |
| % Pd | 1.1 | 0.6 | 0.9 |
| % M | 0 | 0.8 | 2.6 |
| HC Yield, % (3) | 13 | 7 | 7 |
| HC Sel., % (3) | | | |
| C$_1$ | 28 | 18 | 23 |
| C$_2$ | 34 | 51 | 35 |
| C$_3$ | 28 | 27 | 30 |
| C$_4$ | 10 | 4 | 12 |
| C$_{5+}$ & Ar | 0 | 0 | 0 |
| CO$_2$ Yield (3) | 13 | 6 | 9 |

(1) 350° C., H$_2$/CO = 1, 735 psig (5169 kPa), Actual Hourly Space Velocity = 80
(2) Added as salts to composition growth mixture
(3) Based on carbon The data show that composition 2 of the present invention has a higher C$_2$ selectivity than composition D or 3 for synthesis gas conversion when tested at 350° C.

EXAMPLE 9

This example compares the catalytic properties of the palladium ferrometallosilicate compositions (2 and 3) of the present invention to the composition (D) for the conversion of synthesis gas. All of the compositions were prepared in accordance with Example 1 and all runs were conducted at 735 psig (5169 kPa) in a 310 stainless steel tubular reactor at an actual hourly space velocity of 80.

TABLE VI

SYNGAS REACTIONS
THE EFFECT OF METAL
ON PALLADIUM FERROSILICATES,
Pd—SiO$_2$/FeO$_x$/MO$_x$(1)

| Composition | D | 2 | 3 |
|---|---|---|---|
| M(2) | | Al | Ti |
| HC Yield, % (3) | 26 | 19 | 19 |
| HC sel, % (3) | | | |
| C$_1$ | 46 | 33 | 36 |
| C$_2$ | 39 | 47 | 61 |
| C$_3$ | 12 | 17 | 3 |
| C$_4$ | 3 | 2 | 0 |
| C$_{5+}$ & Ar | 0 | 0 | 0 |
| CO$_2$ Yield (3) | 23 | 16 | 16 |

(1) 400° C., H$_2$/CO = 1, 735 psig, Actual Hourly Space Velocity = 80
(2) Added as salts to composition growth mixture
(3) Based on carbon The data show that increasing the reaction temperature of compositions (2 and 3) enhances ethane selectivity which is higher than D.

EXAMPLE 10

This example compares the effects of acid extraction on palladium ferroaluminosilicate compositions (2 and 4) in terms of the effect on catalytic activity for synthesis gas conversion and ethane selectivity. All of the compositions were prepared in accordance with Example 1 and all runs were conducted at 735 psig (5169 kPa) in a 310 stainless steel tubular reactor at an actual hourly space velocity of 80.

TABLE VII
SYNGAS REACTIONS
THE EFFECT OF EXTRACTION
ON THE CATALYTIC PROPERTIES
OF PALLADIUM FERROALUMINOSILICATE

| Composition | 2 | 4 |
|---|---|---|
| Extracted (2) | No | Yes |
| % Fe | 1.5 | 0.8 |
| % Pd | 0.6 | 1.1 |
| % Al | 0.8 | 0.7 |
| HC Yield, % (3) | 19 | 20 |
| HC Sel., % (3) | | |
| $C_1$ | 33 | 24 |
| $C_2$ | 47 | 61 |
| $C_3$ | 17 | 13 |
| $C_4$ | 2 | 2 |
| $C_{5+}$ & Ar | 0 | 0 |
| $CO_2$ Yield, % (3) | 16 | 15 |

(1) 400° C., H₂/CO = 1, 735 psig (5169 kPa), Actual Hourly Space Velocity = 80
(2) 1N HCl, 60° C., 24 hours before Pd-exchange
(3) Based on Carbon The data show the desirability of extracting the compositions with hydrochloric acid to enhance ethane selectivity for synthesis gas conversion. Composition 4 shows an increased selectivity for ethane over composition 2 which is believed to be related to the lower iron content of the composition or the removal of non-lattice iron.

EXAMPLE 11

This example compares the catalytic properties of a palladium ferrotitanosilicate composition of the present invention and the effect of sodium content on the catalytic activity. All of the compositions were prepared in accordance with Example 1 and all runs were conducted at 735 psig (5169 kPa) in a 310 stainless steel tubular reactor at an actual hourly space velocity of 80.

TABLE VIII
SYNGAS REACTIONS
EFFECT OF SODIUM ION ON Pd—SiO₂/FeOₓ/TiOₓ

| Composition | 5 | 6 |
|---|---|---|
| Ion Form (2) | NH₄⁺ | Na⁺ |
| Na, Wt % | 0.05 | 0.79 |
| HC Yield, %.(3) | 18 | 17 |
| HC Sel., %.(3) | | |
| $C_1$ | 38 | 90 |
| $C_2$ | 57 | 10 |
| $C_3$ | 5 | 0 |
| $C_4$ | 0 | 0 |
| $C_5$ | 0 | 0 |
| Ar | 0 | 0 |
| $CO_2$ Yield, 9.(3) | 16 | 14 |

(1) 400° C., H₂/CO = 1, 735 psig, (5169 kPa), Actual Hourly Space Velocity = 80
(2) Ion Form of Catalyst which was Pd-exchanged
(3) Based on carbon The data show that composition 5, which was NH₄⁺ exchanged and then palladium exchanged has a higher ethane selectivity than composition 6 which was only palladium exchanged. The lower ethane selectivity is believed to be due to the higher sodium content of composition 6.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for the conversion of synthesis gas comprising:
    contacting synthesis gas which comprises hydrogen and carbon monoxide with a catalytically effective amount of a crystalline ferrometallosilicate composition represented in terms of mole ratios as follows:

$$(0.2 \text{ to } 15)M_{\frac{2}{m}}O : (0.2 \text{ to } 10)Z_{\frac{2}{z}}O : (5 \text{ to } 1000)SiO_2 :$$

$$Fe_{\frac{2}{n}}O : (0 \text{ to } 2000)H_2O$$

wherein M comprises a cation of a quaternary ammonium, metal, ammonium, hydrogen and mixtures thereof, m is the valence of said cation, n is the valence of the iron cation, Z is aluminum, titanium or manganese and z is the valence of the Z cation,
    wherein said composition contains ion-exchanged palladium or palladium impregnated onto said composition, and
    said contacting is conducted under conversion conditions effective to provide an ethane selectivity of at least 45% when Z is aluminum or titanium and a C₃ selectivity of at least 35% when Z is manganese.

2. A method according to claim 1 wherein the composition is substantially sodium free.

3. A method for the conversion of synthesis gas comprising:
    contacting synthesis gas which comprises hydrogen and carbon monoxide with a catalytically effective amount of a crystalline ferrometallosilicate composition prepared by a method which comprises:
    (a) heating a reaction mixture capable of forming a crystalline product under conditions effective to provide a crystalline product, said reaction mixture comprising a quaternary ammonium compound, a source of an aluminum oxide, titanium oxide or manganese oxide, an oxide of silicon, an alkali metal hydroxide, a source of iron oxide, and water,
    (b) recovering the crystalline product, and
    (c) ion-exchanging the recovered crystalline product with a palladium salt solution to provide a palladium ion-exchanged crystalline ferrometallosilicate,
    wherein said contacting is conducted under conversion conditions effective to provide an ethane selectivity of at least 45% when said reaction mixture comprises aluminum oxide or titanium oxide and a C₃ selectivity of at least 35% when said reaction mixture comprises manganese oxide.

4. A method according to claim 3 wherein said reaction mixture additionally contains a chelating agent.

5. A method according to claim 4 wherein said chelating agent is 8-hydroxyquinoline-5-sulfonic acid or urea.

6. A method according to claim 3 wherein said quaternary ammonium compound is tetrapropylammonium bromide, said source of aluminum oxide is aluminum chloride or aluminum hydroxide, said source of titanium oxide is titanium chloride, said source of manganese oxide is manganese sulfate, manganese chloride or manganese nitrate, said oxide of silicon is fumed silica, said alkali metal hydroxide is sodium hydroxide and said source of iron oxide is ferrous chloride, ferric chloride or mixtures thereof.

7. A method according to claim 3, including the following additional step:
(d) calcining the palladium ion-exchanged crystalline ferrometallosilicate in air at a temperature of about 300° C. to about 600° C. for at least 4 hours.

8. A method according to claim 7, including the following additional steps:
(e) heating the calcined palladium ferrometallosilicate in the presence of hydrogen from ambient temperature to an elevated temperature of about 300° C. to about 400° C. at a rate of temperature increase of about 0.5° to about 2° C. per minute;
(f) maintaining said silicate at said temperature for about 0.75 to about 1.25 hour; and
(g) cooling said silicate to ambient temperature in the presence of hydrogen.

9. A method according to claim 3, including the following additional step:
(h) mixing said silicate with a methanol synthesis catalyst.

10. A method according to claim 9 wherein said methanol catalyst comprises chrominum oxide-zinc oxide or copper oxide-zinc oxide.

* * * * *

UNITED STATES PATENT AND TRADEMARK OFFICE
CERTIFICATE OF CORRECTION

PATENT NO. : 4,670,474

DATED : June 2, 1987

INVENTOR(S) : James A. Hinnenkamp and Vernon V. Walatka

It is certified that error appears in the above-identified patent and that said Letters Patent is hereby corrected as shown below:

Claim 3, line 14, delete "and", insert --(c) heating the recovered crystalline product in an inert atmosphere or air at 200-900°C for 1 to 60 hours, and--; line 15, "(c)" should read --(d)--, "recovered" should read --heat-treated--.

Claim 7, line 3, "(d)" should read --(e)--.

Claim 8, line 3, (e)" should read --(f)--; line 8, "(f)" should read --(g)--, line 10, "(g)" should read --(h)--.

Claim 9, line 3, "(h)" should read --(i)--.

Signed and Sealed this

Third Day of November, 1987

*Attest:*

DONALD J. QUIGG

*Attesting Officer*   *Commissioner of Patents and Trademarks*